United States Patent [19]

Bonnet

[11] 4,250,873
[45] Feb. 17, 1981

[54] ENDOSCOPES

[75] Inventor: Ludwig Bonnet, Knittlingen, Fed. Rep. of Germany

[73] Assignee: Richard Wolf GmbH, Fed. Rep. of Germany

[21] Appl. No.: 897,060

[22] Filed: Apr. 17, 1978

[30] Foreign Application Priority Data

Apr. 26, 1977 [DE] Fed. Rep. of Germany ... 7713059[U]

[51] Int. Cl.$^3$ .............................................. A61B 1/00
[52] U.S. Cl. ........................................ 128/7; 128/341
[58] Field of Search ........................................ 128/3–8,
128/349 R, 350 R, 303 R, 305.3, 330, DIG. 25,
341, 344, 345, 325, 303.11, 303.15, 303 A,
241–244

[56] References Cited

U.S. PATENT DOCUMENTS

| | | | |
|---|---|---|---|
| 3,888,258 | 6/1975 | Akiyama | 128/350 R X |
| 3,903,895 | 9/1975 | Alley et al. | 128/350 R |
| 3,989,049 | 11/1976 | Yoon | 128/325 X |

FOREIGN PATENT DOCUMENTS 7336834 10/1973 Fed. Rep. of Germany .............. 128/7

Primary Examiner—Robert W. Michell
Assistant Examiner—Jeffrey W. Tayon
Attorney, Agent, or Firm—Kinzer, Plyer, Dorn & McEachran

[57] ABSTRACT

This invention relates to endoscopes comprising for inserting an implant liner into an opening through a stricture in the urethra.

According to the invention, the endoscope comprises the following features:
(a) an outer barrel, a tensioning tube displaceable axially in the distal direction within said outer barrel against resilient means with radial clearance, an external annular ridge and longitudinal slots at the distal end of said tensioning tube the sections of said tube situated between said slots being arranged to spring radially inwards,
(b) a holding tube which extends through said tensioning tube to receive a telescope said holding tube being fixed in relation to said outer barrel, and having a distal portion of reduced diameter, and an annular ridge adjacent its distal end, and
(c) an implant liner which comprises a distal bush and a proximal bush between which are bridges formed by strips which are sprung to arch outwards, the inside diameter of said distal bush being smaller than the external diameter of said annular ridge on said distal section of reduced diameter of the said holding tube, and the inside diameter of said proximal bush being such that the bush can be inserted over said annularly ridge of said tensioning tube when the latter is sprung inwards and its outside diameter being such that it is carried in the barrel fitted into the distal end thereof.

3 Claims, 4 Drawing Figures

ENDOSCOPES

BACKGROUND OF THE INVENTION

As men become older, the actual urethra often becomes smaller in diameter and this may result in the retention of urine, thus compelling the doctor responsible for treatment to slit the urethra at the point where the constriction is situated, i.e. to perform what is known as the opening of a stricture. Since the wound contracts in the course of healing, there is a danger that the open passage through the urethra which has been created will grow together again or will become very much restricted.

To prevent the opening through the stricture growing together again this way, it has already been suggested that an implant liner be inserted in the opening through the stricture by means of an endoscope. The implant liner remains in the opening until the wound has healed and is then withdrawn again through the urethra from the healed opening by means of the endoscope. In this known endoscope, in addition to a telescope having a light conductor, there is also a parallel tube extending through the barrel of the endoscope, for a longitudinally displaceable shaft having forceps jaws at the distal end which spread open resiliently and by means of which an implant liner is gripped, inserted through the urethra and placed in the opening through the stricture, where it is released by moving the shaft of the forceps.

The liner advantageously consists of plastics material and it has been found extremely difficult to insert it because the telescope is situated alongside the guide for the forceps jaws, and also that with this design the barrel of the endoscope is of undersirably large diameter.

It is an object of the invention to enable a liner to be safely inserted in an opening through a stricture which has previously been made by slitting, while at all times under satisfactory observation and using a barrel of reduced diameter.

SUMMARY OF THE INVENTION

To enable this and other objects to be achieved, the invention provides an endoscope for introducing an implant liner into an opening through a stricutre in the urethra which comprises the following constituent parts:

(a) an outer barrel in which a tensioning tube is displaceable axially in the distal direction against resilient means with radial clearance, said tube being provided at the distal end with an external annular ridge and longitudinal slots, the sections of the tube situated between the slots being designed to spring radially inwards, (b) a holding tube which extends through the tensioning tube to receive the telescope, which is fixed in relation to the barrel, which has a distal portion of reduced diameter, and which has an annular ridge adjacent its distal end, (c) and an implant liner which comprises two bushings between which are bridges formed by strips which are sprung to arch outwards, the inside diameter of the bushings at the distal end being smaller than the external diameter of the annular ridge on the distal section of reduced diameter of the holding tube and the inside diameter of the bush at the proximal end being such that the bushing can be inserted over the annularly ridged end of the tensioning tube when the latter is sprung inwards and its outside diameter being such that is carried in the barrel, fitted into the distal end thereof.

With this construction, the telescope and its light conductor extend centrally through the holding tube, so that the liner can be accurately inserted in the opening through the stricture while under proper observation, using an endoscope which is of comparatively small diameter as a result of the holding tube being mounted in the tensioning tube and the tensioning tube in the barrel the implant liner projecting only slightly or not at all beyond the diameter of the barrel when inserted through the urethra but being able to open out in the opening through the stricture, as will be described in detail below.

BRIEF DESCRIPTION OF THE DRAWINGS

In order that the invention may be more clearly understood reference will now be made to the accompanying drawings, which show one embodiment thereof by way of example, and in which.

DETAILED DESCRIPTION OF THE PREFERRED EMBODIMENT

Figure 1:
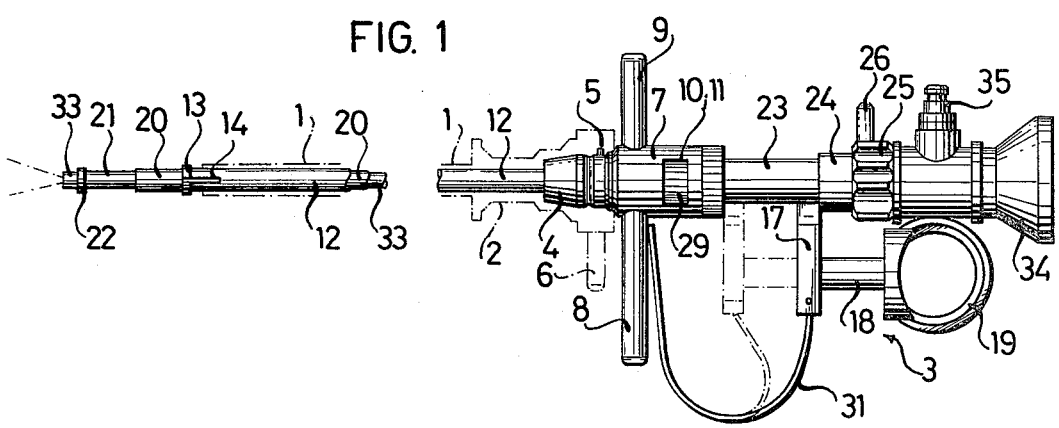
FIG. 1 is a side-view of an endoscope for inserting an implant liner in an opening through a stricture in the urethra.

Referring now to the drawings, these show an endoscope for use in the urethra, which comprises a barrel 1 (indicated in chain lines) having a proximal machined part 2, and a unit 3 which can be locked to the barrel by a bayonet coupling using a taper 4, a pin 5 and a handle 6, or in other way found suitable. On the machined part 2, the barrel 1 has opposing cocks for the inflow and outflow of irrigating water.

The unit 3 comprises a tapered part 7 having two opposing finger grips 8 and 9 and contains two opposing apertures 10 and 11 lying at 90° to the finger girps 8, 9. Through the tapered part 7 extends a tensioning tube 12 having a distal annular ridge 13. At the distal end the tensioning tube is provided with for example four longitudinal slots 14 uniformly distributed around its circumference, and the sections of tube between the slots are designed to spring radially inwards. Proximally, a reinforcing tube 15 is soldered onto the tensioning tube 12 and towards the distal end is it formed as a tubular threaded shank 16. At the proximal end, the reinforcing tube 15 is provided with a fixed arm 17 to which a finger loop 19 is connected via a shank 18. The shank 18 may be rotatably secured to the arm 17 for comfort in use.

Extending co-axially through the tensioning tube 12 is a holding tube 20 which is of somewhat reduced diameter along a distal section 21 and which has an annular ridge 22 adjacent its distal end. Proximally, the holding tube 20 is permanently connected via a guide tube 23 to a terminal part 24 having an internal taper and in the distal direction it passes through the turned part 7. Between the distal end of the guide tube 23 and the tubular threaded shank 16, which advantageously has a multiple-start external thread, a freely rotatable knurled nut 29 is mounted on the reinforcing tube 15. This nut can be turned through the two lateral apertures 10, 11 and can be engaged with the external thread on the tubular shank 16, as will be explained below. Connected to the terminal part 24 is a bayonet collar 25 having a handle 26, to allow the telescope 33, which has an eye-piece 34 and a lateral connector 25 for a light conductor to be coupled on. In the rest position shown in FIG. 1, the telescope 33 projects slightly from the distal end of the holding tube 20. The arm 17 connected to the reinforcing tube 15 is connected to the finger grip 8 by a compression spring, e.g. a leaf spring 31, and projects through a longitudinal slot 28 in the guide tube 23. The compression spring 31 forces the reinforcing tube 15 and thus the tensioning tube 12 to an extreme proximal position which is defined in practice by the knurled nut 29, which in the rest position presses against the distal end of the guide tube 23 on one side and the threaded shank 16 on the other.

Figure 2:
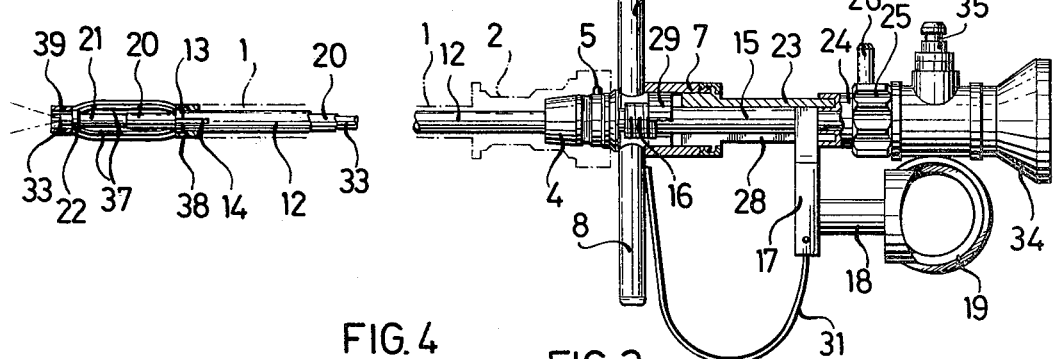
FIG. 2 is a similar side-view, partly in section, showing the implant liner fitted on the distal end of the endoscope.
Figures 3, 4:
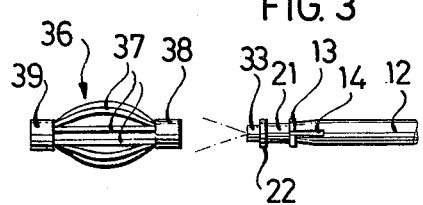
FIG. 3 shows the distal end of the endoscope in the appropriate position for insertion in the implant liner.
FIG. 4 is a side-view of the implant liner.

The implant liner 36 which is used is shown in FIGS. 2 and 4 and comprises two bushings 38 and 39, between which are narrow strips 37 of resilient material which form bridges and which arch outwards to form a sort of cage in the rest position. The narrow strips 37 and the bushings 38 and 39 are coated with a physiologically acceptable plastics material. Of the two bushings, which are of the same outside diameter, the bush 39 at the distal end has an inside diameter which is somewhat smaller than the diameter of the annular ridge 22, while the inside diameter of the bushings 38 is such as to allow the ridge 13 on the tensioning tube 12 to slide through it when the end of the tensioning tube 12 which is provided with the slots 14 is situated in the region of the smaller diameter 21 of the inner holding tube 20.

The way in which operations take place with the endoscope described above is as follows: Beginning from the state shown in FIG. 1, the tensioning tube 12, which carries the reinforcing tube 15, is moved in the distal direction in relation to the holding tube 20 out of the barrel 1 in opposition to the resilient means 31, by pressure from fingers and thumb against the finger grips 8, 9 and 19, until the annular ridge 13 and the sections located between the slots 14 are in the region where the thinner end 21 of the holding tube 20 is situated. Hence, the sections between the slots 14 spring radially inwards, with the result that the diameter of the annular ridge 13 is reduced somewhat, as shown in FIG. 3. With the endoscope in this position the implant liner 36 is inserted on the distal end of the tubes 20 and 12 until the ridge 22 on the inner holding tube 20 rests against the proximal end of the bush 39, while the ridge 13 slides through the bush 38 and as it does so the liner 36 is slid over the tensioning tube 12 and the bush 38 engages in the distal end of the barrel 1. The pressure from the fingers against the grips 8, 9 and 19 is now relaxed and the spring 31 thus moves the tensioning tube 12 in the proximal direction, the sections of tube between the slots 14 at the distal end being forced outwards again by the thicker part of the holding tube 20 and the ridge 13 then applying itself to the inner distal end of bush 38. In this way the implant liner 36 is firmly connected to the distal end of the endoscope, but the strips 37 of the implant liner are arched outwards and are thus of greater diameter than the barrel 1. To reduce the strips 37 to the same or approximately the same, diameter as the barrel 1, the knurled nut 29 is now engaged with the thread on the tubular threaded shank 16 and is turned, thus drawing the reinforcing tube 15 and the tensioning tube 12 somewhat further into the barrel 1 in the proximal direction, the ridge 13 then carrying bush 38 with it while bush 39 is held statinary by ridge 22. In this way, the strips 37 of the implant liner 36 are straightened out to the same, or approximately the same, diametric size as the barrel 1. The endoscope and the implant liner are then pushed along the urethra to the opening through the stricture and pressure from the fingers is then again exerted on the grips 8, 9 and 19, in opposite to the spring 31, so that the diameter of the annular ridge 13 on the tensioning tube 12 reduces as shown in FIG. 3, whereby the distal end of the endoscope can be withdrawn from the implant liner 36 and at the same time the whole instrument can be withdrawn from the urethra. At the same time the liner spreads open, as a result of the strips 37 arching outwards, and enlarges the opening through the stricture accordingly. To withdraw the implant liner once the wound formed by the opening through the stricture has healed, the reverse procedure is adopted.

I claim:

1. An endoscope for inserting an implant liner into an opening through a stricture in the urethra, said endoscope comprising a telescope for viewing internal anatomy and further comprising the following:
   (a) an outer barrel having a telescope eyepiece at the proximal end thereof which is remote from the opposite or distal end, a tensioning tube having both proximal and distal ends and being displaceable axially in the distal direction within said outer barrel and against a resilient means, said resilient means being suspended from said outer barrel, and external annular ridge and longitudinal slots at the distal end of said tensioning tube and the sections of said tube situated between said slots being arranged to spring radially inwards,
   (b) a holding tube having a proximal end and a distal end, and said holding tube having a proximal portion and a distal portion, and which extends through said tensioning tube to receive the telescope, and said holding tube being fixed in relation to said outer barrel, said distal portion of said holding tube being of reduced diameter, and there being an annular ridge adjacent the distal end of said holding tube, and
   (c) an implant liner which comprises a distal bushing and a proximal bushing between which are resilient bridges formed by strips which are sprung to arch outwards, the inside diameter of said distal bushing being smaller than the external diameter of said annular ridge on said distal portion of reduced diameter of the said holding tube, and the inside diameter of said proximal bushing being such that said proximal bushing can be inserted over said annular ridge of said tensioning tube, and the outside diameter of said proximal bushing being such that the proximal bushing is carried in the barrel by being fitted into the distal end thereof.

2. An endoscope according to claim 1, which further comprises finger and thumb grips, a reinforcing tube receiving said tensioning tube and a guide receiving said reinforcing tube, and wherein said reinforcing tube is connected via a longitudinal slot to said thumb grip which, in common with said tensioning tube, is biased by a compression spring constituting said resilient means.

3. An endoscope according to claim 2, wherein said reinforcing tube has a distal end and, towards its distal end, a tubular shank having an external thread with which is engageable a knurled nut freely rotatable on said reinforcing tube with some axial play.

* * * * *